(12) United States Patent
Kim

(10) Patent No.: US 10,306,987 B2
(45) Date of Patent: Jun. 4, 2019

(54) SWING CHAIR

(71) Applicant: DESIGN PARK DEVELOPMENT CO., LTD., Seoul (KR)

(72) Inventor: Yo Seob Kim, Gimpo-si (KR)

(73) Assignee: DESIGN PARK DEVELOPMENT CO., LTD., Seoul (KR)

( * ) Notice: Subject to any disclaimer, the term of this patent is extended or adjusted under 35 U.S.C. 154(b) by 0 days.

(21) Appl. No.: 15/574,485

(22) PCT Filed: Feb. 16, 2017

(86) PCT No.: PCT/KR2017/001679
§ 371 (c)(1),
(2) Date: Nov. 16, 2017

(87) PCT Pub. No.: WO2018/084386
PCT Pub. Date: May 11, 2018

(65) Prior Publication Data
US 2018/0289161 A1  Oct. 11, 2018

(30) Foreign Application Priority Data

Nov. 4, 2016  (KR) ........................ 10-2016-0146545
Dec. 15, 2016  (KR) ........................ 10-2016-0171400
Jan. 18, 2017  (KR) ........................ 10-2017-0008861

(51) Int. Cl.
*A63G 9/12* (2006.01)
*A47D 9/02* (2006.01)
(Continued)

(52) U.S. Cl.
CPC .............. *A47C 3/0255* (2013.01); *A47C 7/62* (2013.01); *A47C 11/00* (2013.01); *A47D 9/02* (2013.01);
(Continued)

(58) Field of Classification Search
CPC ... A63G 9/00; A63G 9/04; A63G 9/12; A63G 9/16; A47C 3/0255; A47C 13/00; A47C 17/84; A47D 13/00; A47D 13/105
(Continued)

(56) References Cited

U.S. PATENT DOCUMENTS

| 109,165 A | 11/1870 | Winston |
| 160,390 A | 3/1875 | Cain |

(Continued)

FOREIGN PATENT DOCUMENTS

| KR | 20-0228143 Y1 | 6/2001 |
| KR | 10-2006-0037130 A | 5/2006 |

OTHER PUBLICATIONS

International Search Report for PCT/KR2017/001679 dated Jul. 20, 2017 from Korean Intellectual Property Office.

*Primary Examiner* — Kien T Nguyen
(74) *Attorney, Agent, or Firm* — Revolution IP, PLLC

(57) ABSTRACT

A swing chair includes: a support which is installed at a certain height or more above the floor; a main operation member elongated and having a virtual first rotation axis provided to the support at one side thereof and rotatably coupled to the support; a sub operation member elongated and having a virtual second rotation axis, provided to the support at one side thereof and spaced parallel to the first rotation axis, and rotatably coupled to the support; a seat portion coupled to any one of the main operation member and the sub operation member; and a rotation connecting member elongated and arranged in a front-rear direction and having a rear portion that is rotatably coupled to the other side of the main operation member and a front portion that is rotatably coupled to the other side of the sub operation member.

25 Claims, 12 Drawing Sheets

(51) Int. Cl.
      *A47C 3/025*    (2006.01)
      *A47C 7/62*     (2006.01)
      *A47C 11/00*    (2006.01)
      *A61H 15/00*    (2006.01)
      *A61H 23/02*    (2006.01)
      *A61H 39/04*    (2006.01)
      *A61B 5/00*     (2006.01)
      *A63G 9/16*     (2006.01)
      *A47D 9/04*     (2006.01)

(52) U.S. Cl.
      CPC ............. *A47D 9/04* (2013.01); *A61B 5/00* (2013.01); *A61B 5/6891* (2013.01); *A61H 15/0078* (2013.01); *A61H 23/02* (2013.01); *A61H 39/04* (2013.01); *A63G 9/12* (2013.01); *A63G 9/16* (2013.01); *A61H 2201/0149* (2013.01); *A61H 2201/1669* (2013.01); *A61H 2201/1676* (2013.01)

(58) Field of Classification Search
      USPC ............. 472/118, 120–125; 297/273, 433
      See application file for complete search history.

(56) References Cited

U.S. PATENT DOCUMENTS

| | | | | |
|---|---|---|---|---|
| 1,107,341 A | * | 8/1914 | Oldfield | A47C 3/0255 297/273 |
| 1,259,061 A | * | 3/1918 | Whetstone | A47C 13/00 297/118 |
| 4,456,244 A | | 6/1984 | Andrews | |
| 4,799,669 A | * | 1/1989 | Appleton | A63G 9/00 297/277 |

* cited by examiner

SWING CHAIR

TECHNICAL FIELD

The present invention relates to a swing chair, and more particularly, to a swing chair which easily swings by an external force of a user even without a separate power source.

BACKGROUND ART

In a general swing, a user is seated in a seat portion and shakes the entire body forward/rearward to generate an inertial force so as to rotate the swing forward or rearward.

However, in the general swing, a process in which the swing is rotated rearward at an initial time in order to obtain an inertial force, and is then moved forward should be repeatedly performed, and at the same time, legs should be shaken forward or rearward to maintain the inertial force. Thus, it is difficult and inconvenient to use the swing.

Further, in a generally-used automatically-shaken swing, because a separate driving device such as a motor, complex gears, and the like are added to the swing to rotate the swing, a configuration of the swing is complex, manufacturing costs thereof increase, and separate electricity charges are charged.

Thus, a method for solving the above problems is required.

DISCLOSURE

Technical Problem

The present invention has been conceived to solve the above-described problems, and a swing chair includes a support, a main operation member, a sub operation member, a seat portion, and a rotation connecting member, so that an operation structure for the swing chair is simplified.

The support, the main operation member, the sub operation member, and the rotation connecting member are arranged to form a virtual sealed quadrangle, so that the main operation member and the seat portion are interlocked with each other according to the virtual quadrangle to be moved forward about the first rotation axis.

With respect to the third rotation axis, the length of a front portion of the rotation connecting member is large and the length of a rear portion of the rotation connecting member is small. Thus, according to the principle of the lever, even when a user applies a small force, the rotation connecting member is rotated by a large force, and thus, the seat portion in which the user is seated is easily moved forward, so that the swing chair may be used for lower body exercise of the elderly person.

A separate operation handle is provided in the rotation connecting member, and the user moves the operation handle in a front-rear direction without stepping on a foothold, so as to swing the seat portion in the front-rear direction.

A handle is installed in the seat portion or the rotation connecting member, so that a guardian swings the swing chair in which the child or the elderly person is seated, in the front-rear direction using the handle.

The main operation member or the sub operation member is selectively formed in the shape of a wire or a frame, so that the swing chair having various forms may be manufactured.

Problems of the present application are not limited to the above-described problems, and yet other non-mentioned problems could be clearly understood by those skilled in the art with reference to the following descriptions.

Technical Solution

In order to achieve the above aspects, it is preferable that a swing chair according to the present invention includes a support which is installed at a certain height or more above the floor, a main operation member which is elongated and has a virtual first rotation axis provided to the support at one side thereof and which is rotatably coupled to the support, a sub operation member which is elongated and has a virtual second rotation axis spaced parallel to the first rotation axis, and which is rotatably coupled to the support, a seat portion coupled to either of the main operation member or the sub operation member, and a rotation connecting member which is elongated and arranged in a front-rear direction and has a rear portion that is rotatably coupled to the other side of the main operation member and a front portion that is rotatably coupled to the other side of the sub operation member so that a closed virtual quadrangle is formed together with the support, the main operation member, and the sub operation member, wherein an angle of coupling between the rotation connecting member and the main operation member is changed according to user's operation and the main operation member is interlocked with the virtual quadrangle and swings forward and backward based on the first rotation axis.

It is preferable that a portion of the rotation connecting member protrudes forward in a longitudinal direction.

It is preferable that the rotation connecting member vertically swing about a point of coupling between the rotation connecting member and the sub operation member.

It is preferable that when an external force is applied to a front portion of the rotation connecting member to rotate the rotation connecting member rearward, an interior angle of coupling between the rotation connecting member and the main operation member increases in the virtual quadrangle.

It is preferable that a coupling position of the rotation connecting member and the sub operation member is adjusted along a longitudinal direction.

It is preferable that the rotation connecting member is extended and contracted along a longitudinal direction.

It is preferable that the rotation connecting member is adjusted in a state in which a user is seated in the seat portion.

It is preferable that a front portion of the rotation connecting member along the longitudinal direction is formed in the shape of a foothold, so that the user operates the rotation connecting member using his/her feet while being seated in the seat portion.

It is preferable that a separate operation handle is provided in front of a point of coupling between the rotation connecting member and the sub operation member, so that the rotation connecting member is arranged at a position where the user approaches the rotation connecting member while being seated in the seat portion.

It is preferable that at least a portion of the main operation member in the longitudinal direction is formed in the shape of a wire.

It is preferable that the seat portion is fixedly coupled to the main operation member.

It is preferable that an area of the main operation member, which is arranged below the seat portion along the longitudinal direction, is formed in the shape of a frame.

It is preferable that the sub operation member is formed in the shape of a wire.

The swing chair may further include a separate auxiliary support member which is elongated, and has one side that is connected to the support and the other side that is connected to the seat portion.

It is preferable that the auxiliary support member is formed in the shape of a wire.

It is preferable that the main operation member is formed in the shape of a frame, and the sub operation member is formed in the shape of a wire.

It is preferable that the seat portion is fixedly coupled to a lower portion of the main operation member.

It is preferable that the seat portion is fixedly coupled to a lower portion of the sub operation member.

It is preferable that the main operation member is formed in the shape of a wire, and the sub operation member is formed in the shape of a frame.

It is preferable that the seat portion is fixedly coupled to a lower portion of the main operation member.

It is preferable that the main operation member and the sub operation member are formed in the shape of a frame.

It is preferable that the first rotation axis and the second rotation axis are spaced apart from each other in a front-rear direction, and are coupled to the support.

It is preferable that a handle is further provided in at least one of the seat portion and the rotation connecting member.

It is preferable that the main operation member is provided in plurality, the main operation members are spaced apart from each other on the first rotation axis, and the seat portion is fixedly coupled between the main operation members.

It is preferable that the sub operation member is provided in plurality, the sub operation members are spaced apart from each other on the second rotation axis, and the seat portion is fixedly coupled between the sub operation members.

The seat portion may further include a cradle.

The seat portion or the rotation connecting member may further include a massage means.

The seat portion may further include a means configured to measure physical information.

Advantageous Effects

A swing chair according to the present invention for solving the above problems has the following effects.

First, a swing chair includes a support, a main operation member, a sub operation member, a seat portion, and a rotation connecting member so that a structure for manufacturing the swing chair may be simplified, and manufacturing costs thereof may be reduced.

Second, even when a user applies a small force to a foothold using the principle of the lever, the swing chair easily swings forward or rearward without a separate power source, so that the swing chair may be used for lower body exercise of the elderly.

Third, a separate operation handle is provided in the rotation connecting member, and the user moves the operation handle in a front-rear direction without stepping on a foothold, so as to swing the seat portion in the front-rear direction.

Fourth, when the user is the child or the elderly person, a guardian moves the handle forward or rearward to swing the swing chair.

Fifth, a cradle is provided in the seat portion, so that the user may care for young babies.

Sixth, a massage means is provided in the seat portion or the rotation connecting member, thereby relieving fatigue of the user.

Seventh, a means configured to measure physical information is provided in the seat portion to recognize a health state of the elderly person.

Effects of the present invention are not limited to the above-described effects, and other not-mentioned effects could be clearly understood by those skilled in the art with reference to the appended claims.

BRIEF DESCRIPTION OF THE DRAWINGS

The above-described abstract as well as the detailed description of embodiments of the present application, which will be described below, could be better understood when read in conjunction with the accompanying drawings. The embodiments are illustrated in the drawings for the purpose of describing the present application. However, it should be understood that the present application is not limited to accurate arrangements and means which are illustrated.

BEST MODE FOR THE INVENTION

Figure 1:
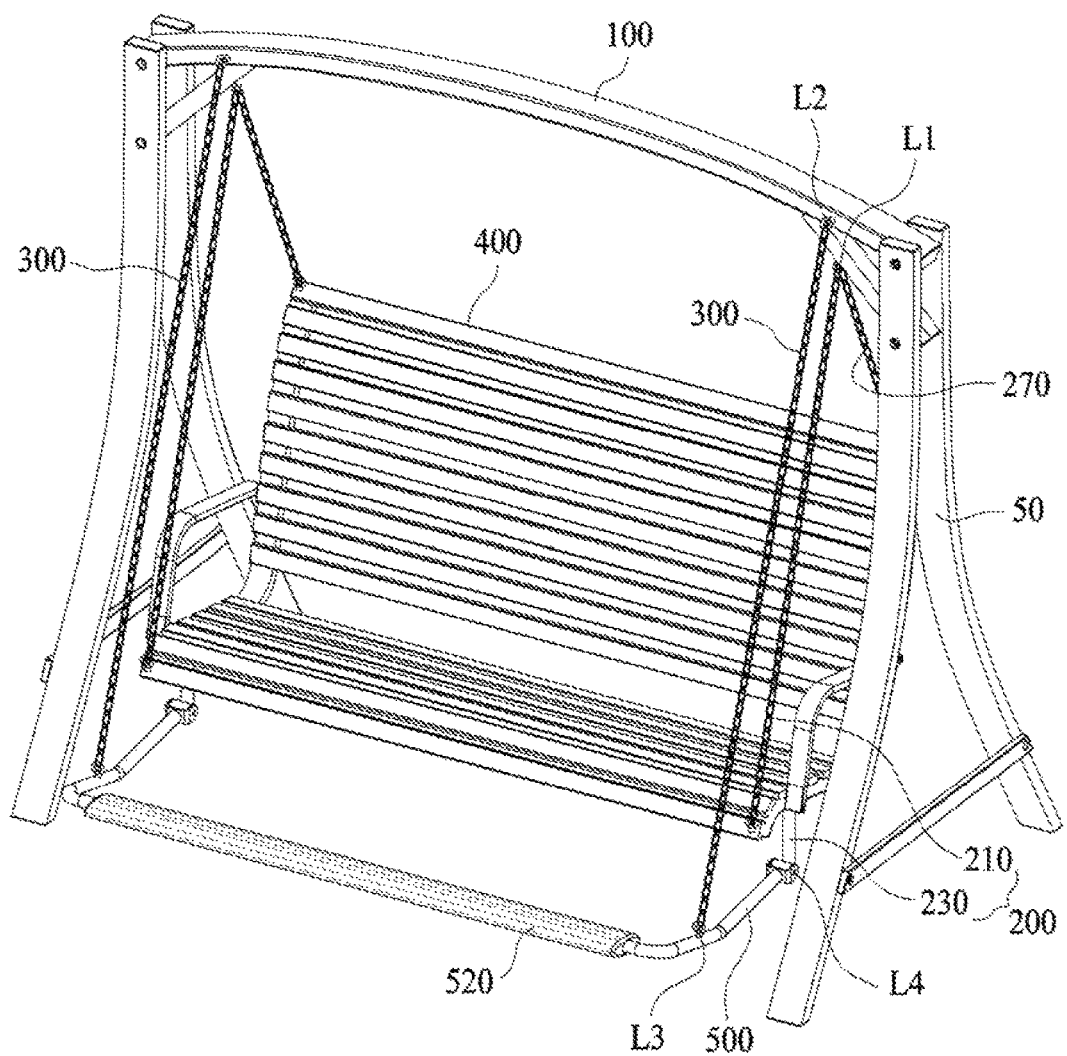
FIG. 1 is a view illustrating the entire shape of a swing chair according to a first embodiment of the present invention.

Hereinafter, exemplary embodiments of the present invention, which may implement the aspects of the present invention in detail, will be described with reference to the accompanying drawings. In description of the present embodiment, the same elements are designated by the same names and the same reference numerals, and additional description according thereto will be omitted. Further, in description of embodiments of the present invention, it is specified that configurations illustrated in the drawings are merely examples for assisting in understanding of the detailed description, the shapes of the configurations may be varied without limitation, and the scope of the rights is not limited due to the detailed description.

Referring to FIG. 1, a swing chair according to the present invention schematically includes a support 100, a main operation member 200, a sub operation member 300, a seat portion 400, and a rotation connecting member 500.

The swing chair according to the present invention may further include pillars 50, and it is preferable that the pillars 50 are installed on a floor to be spaced apart from each other in pairs in consideration of a weight of the swing chair and a weight of a user as in the present embodiment.

The support 100 is installed to connect upper portions of the pillars 50 to each other so as to be located at a certain height or more above the floor.

The support 100 may be installed between a wall and another adjacent wall to be located at a certain height or more above the floor.

Figure 2:
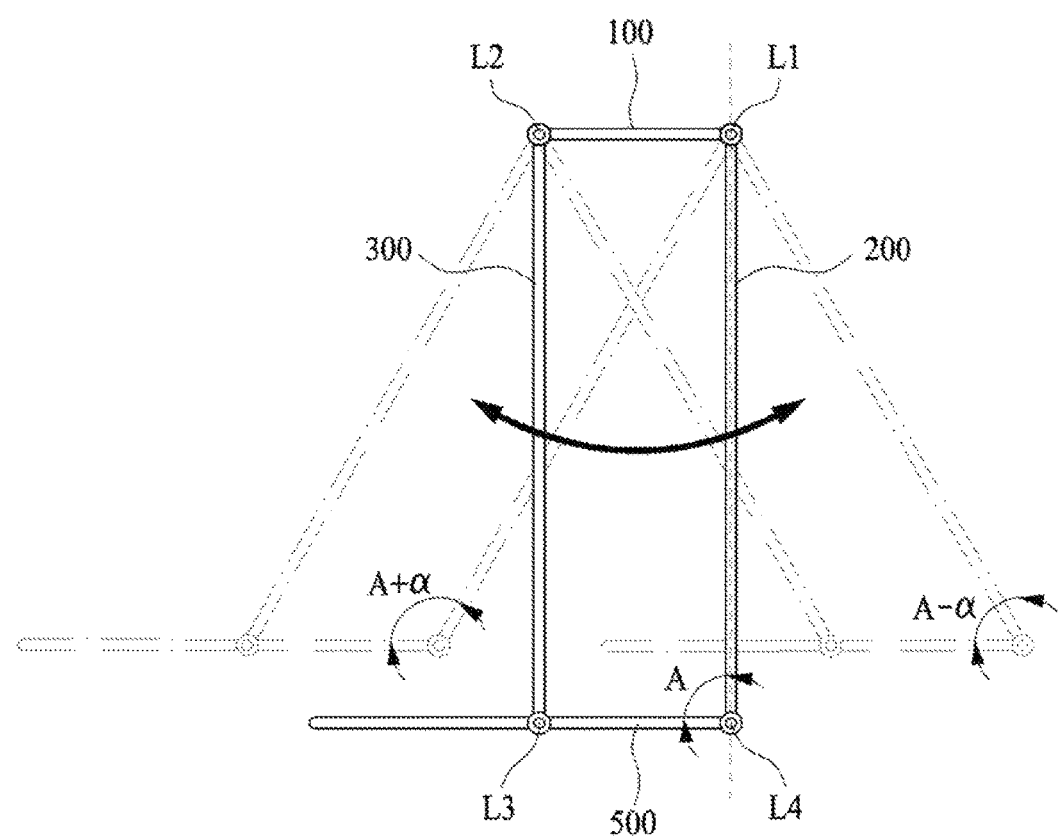
FIGS. 2 and 3 are views illustrating an operation structure which is commonly applied to a swing chair according to first to sixth embodiments of the present invention.
Figure 3:
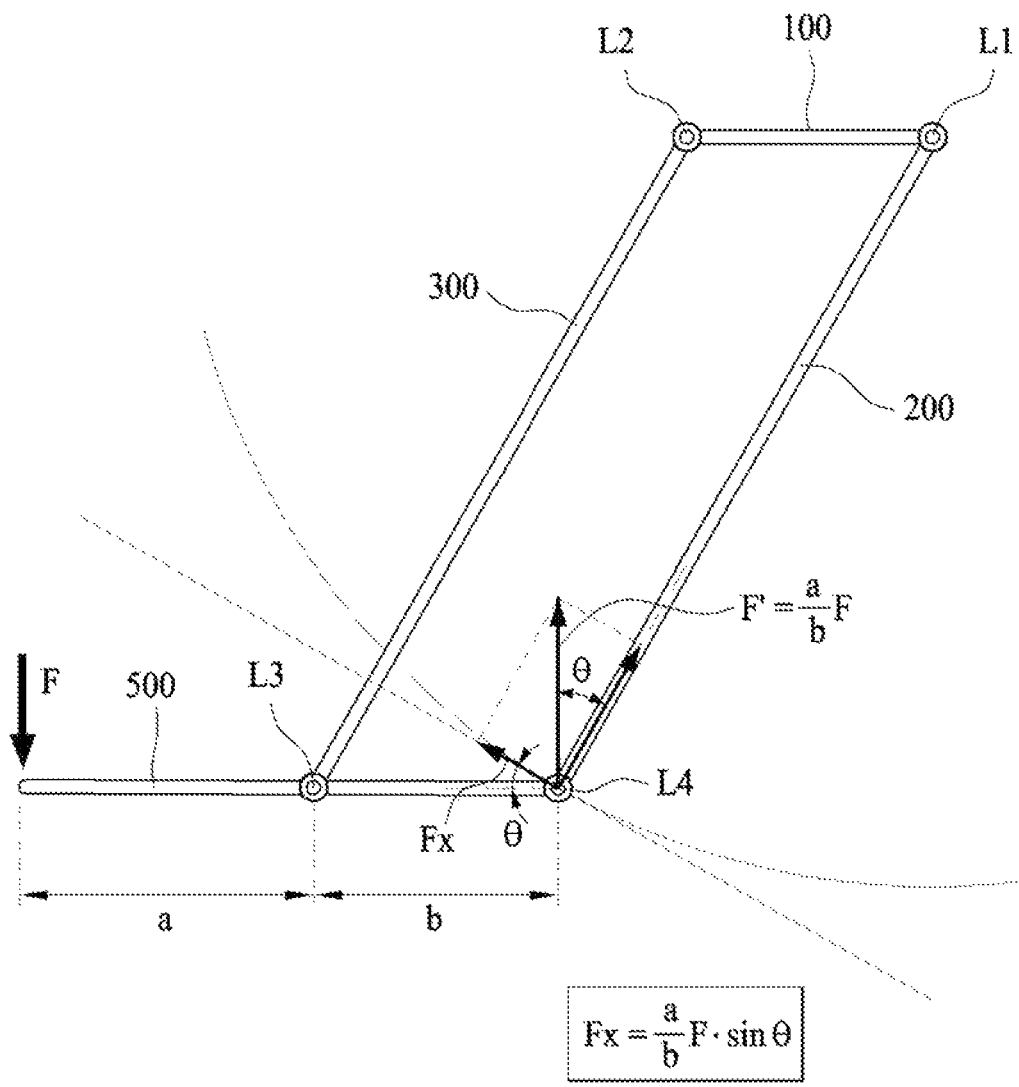
Figure 4:
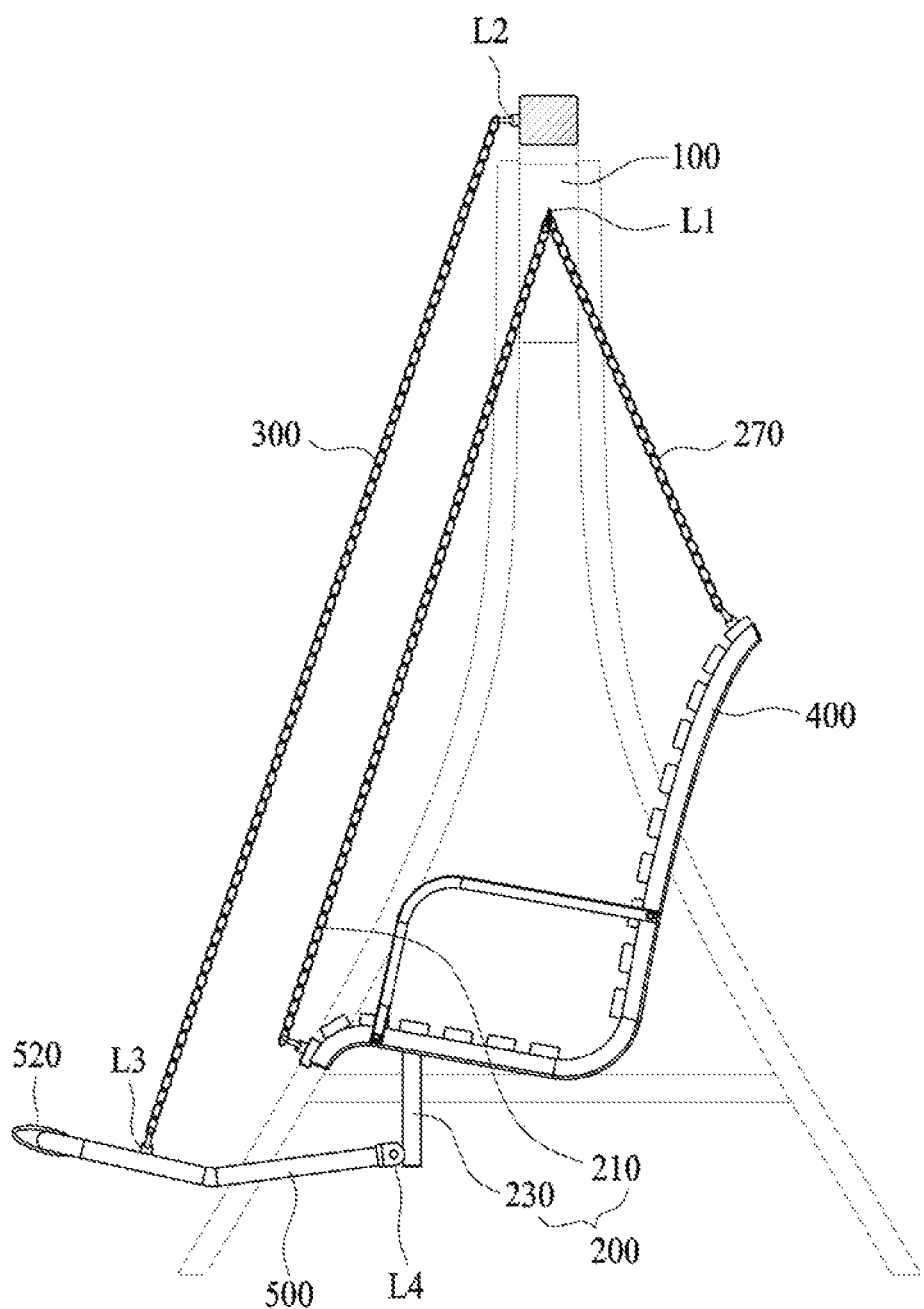
FIGS. 4 to 6 are views illustrating a state in which the swing chair according to the first embodiment of the present invention is operated.
Figure 5:
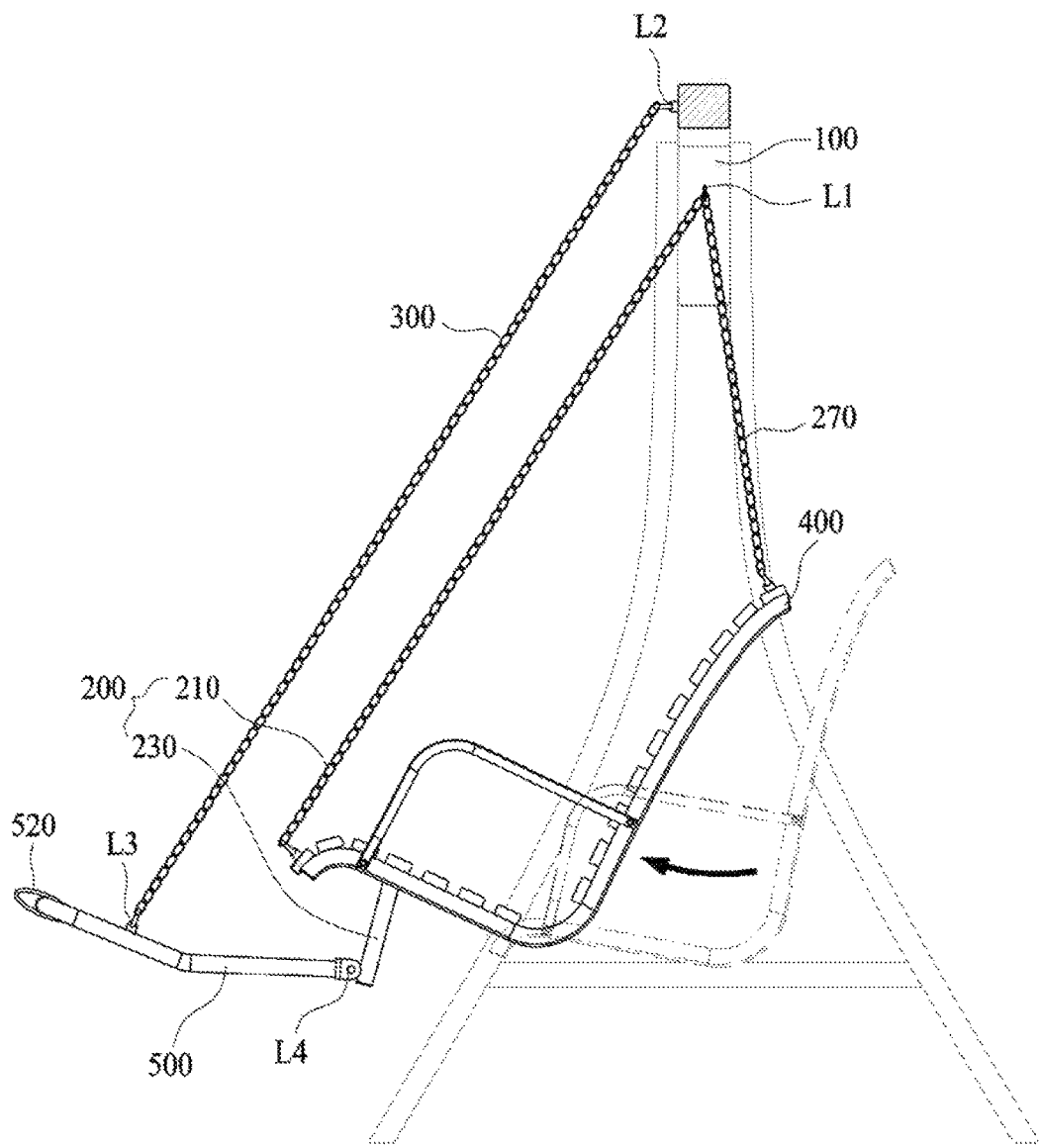
Figure 6:
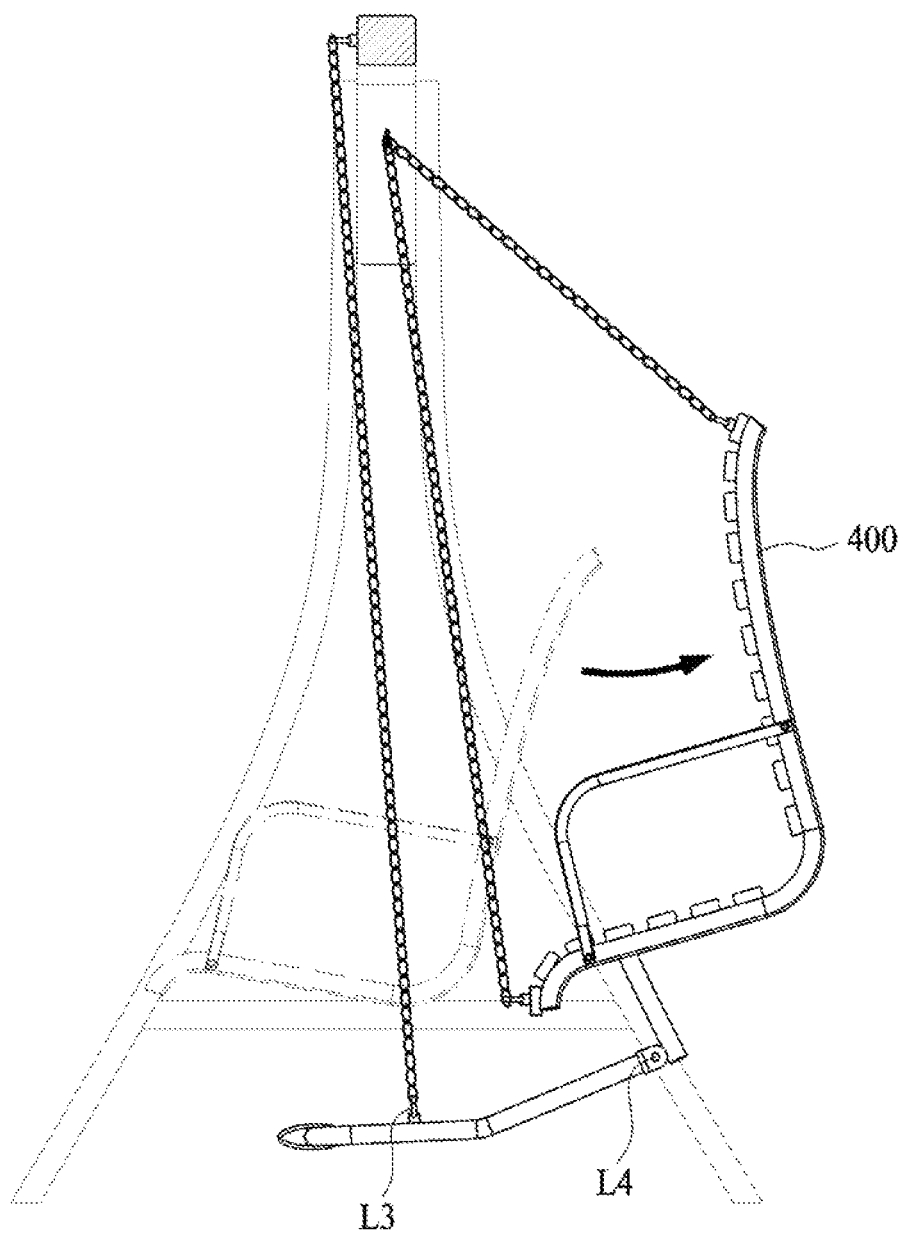

FIG. 1 is a perspective view illustrating a swing chair according to a first embodiment of the present invention, FIGS. 2 and 3 are views illustrating an operation structure which is commonly applied to a swing chair according to first to sixth embodiments of the present invention, and FIGS. 4 to 6 are views illustrating a state in which the swing chair according to the first embodiment of the present invention is operated.

Referring to FIGS. 1 to 4, the main operation member 200 is elongated and is rotatably coupled to the support 100 on one side thereof to have a virtual first rotation axis L1. Further, the main operation member 200 is provided in plurality, and the main operation members 200 are transversely spaced apart from each other on the first rotation axis L1.

The sub operation member 300 is elongated, has a virtual second rotation axis L2 on one side thereof, which is spaced parallel to the first rotation axis L1 by a predetermined distance, and is rotatably coupled to the support 100.

That is, in the present embodiment, the sub operation member 300 is rotatably coupled to the support 100 to be spaced parallel to the first rotation axis L1 on the upper side thereof.

Further, the sub operation member 300 is provided in plurality, and the sub operation members are transversely spaced apart from each other on the second rotation axis L2.

Various rotatable connection means such as a connection hook and a bracket may be used as the virtual first rotation axis L1 and the virtual second rotation axis L2.

Referring to FIGS. 1 and 4, the seat portion 400 is fixed and coupled between the main operation members 200 spaced apart from each other.

At least a portion of the main operation member 200 in the longitudinal direction thereof is formed in the shape of a wire, and an area of the main operation member 200, which is disposed below the seat portion 400 in the longitudinal direction, is formed in the shape of a frame. That is, the main operation member 200 according to the present embodiment includes a wire and a frame.

As illustrated, an upper portion of the main operation member 200 in the form of a wire in the longitudinal direction thereof is rotatably connected to the support 100, and a lower portion of the main operation member 200 in the form of a wire is fixed and coupled to the seat portion 400, and the frame is coupled to a lower portion of the seat portion 400.

Further, an auxiliary support member 270 is further provided such that the seat portion 400 is stably installed in the main operation member 200. The auxiliary support member 270 is elongated in the form of a wire, is rotatably connected to the support 100 on one side thereof, and is connected to the seat portion 400 on the other side thereof.

The rotation connecting member 500 is elongated and arranged in a front-rear direction, is rotatably coupled to the other side of the frame of the main operation member 200 on the rear side thereof to have a virtual fourth rotation axis L4, and is rotatably connected to the other side of the sub operation member 300 on the front side thereof to have a virtual third rotation axis L3. Thus, the rotation connecting member 500 is connected to be vertically rotatable about the third rotation axis L3 serving as a point of coupling between the rotation connecting member 500 and the sub operation member 300.

Various rotatable connection means such as a connection hook and a bracket may be used as the virtual third rotation axis L3 and the virtual fourth rotation axis L4.

Accordingly, as illustrated in FIG. 2, the rotation connecting member 500 is arranged to form a virtual sealed quadrangle together with the support 100, the main operation member 200, and the sub operation member 300.

Further, although not illustrated in the drawing, the entire main operation member 200 may be formed in the shape of a wire. In this case, the seat portion 400 is installed at a lower portion of the main operation member 200 having the form of a wire by using a separate coupling means, and the rear portion of the rotation connecting member 500 is rotatably coupled to the other side of the main operation member 200 having the form of a wire to have the virtual fourth rotation axis L4.

A portion of the rotation connecting member 500 protrudes forward along a longitudinal direction thereof.

In the present embodiment, the rotation connecting member 500 protrudes and extends from the front side of the third rotation axis L3 rotatably coupled to the other side of the sub operation member 300.

As illustrated in FIG. 1, a front portion of the rotation connecting member 500, which protrudes along a longitudinal direction thereof, is formed in the shape of a foothold or a separate foothold 520 is provided in the rotation connecting member 500, so that a user may perform an operation by using his/her foot while being seated in the seat portion 400.

Referring to FIGS. 2, 4, and 5, when the user is seated in the seat portion 400 and transfers an external force for pressing the foothold 520 provided in the rotation connecting member 500, the rotation connecting member 500 is rotated in a direction in which an interior angle A of coupling between the rotation connecting member 500 and the main operation member 200 increases. That is, in a state in which the swing chair is stopped, the rotation connecting member 500 is rotated such that the interior angle A of coupling between the rotation connecting member 500 and the main operation member 200 increases to A+α.

Referring to FIGS. 3 and 5, the rotation connecting member 500 is connected to be vertically rotatable about the third rotation axis L3 serving as a point of coupling between the rotation connecting member 500 and the sub operation member 300.

Here, a distance between the foothold 520 and the third rotation axis L3 refers to a, and a distance between the third rotation axis L3 and the fourth rotation axis L4 refers to b. When the user applies a vertically pressing force F to the foothold 520 of the rotation connecting member 500 while being seated in the seat portion 400, a force F' of vertically lifting up a rear portion of the rotation connecting member 500 is $a/b*F$ based on the principle of the lever "$a*F=b*F'$", and a force $F_x$ of actually rotating the rotation connecting member 500 is $a/b*F*\sin\theta$.

In short, when the user applies the vertically pressing force F to the foothold 520 formed on the front side of the rotation connecting member 500, the rear portion of the rotation connecting member 500 is rotated by the force $F_x$.

Thus, the rotation connecting member 500 is rotated in the direction in which the interior angle A of coupling between the rotation connecting member 500 and the main operation member 200 increases, and the main operation member 200 and the seat portion 400 are interlocked with each other according to the virtual quadrangle and are moved forward about the first rotation axis L1 with respect to a virtual vertical line.

In the swing chair according to the present invention, the rotation connecting member 500 may be extended and contracted forward along the longitudinal direction thereof. That is, a length a between the third rotation axis L3 and a front distal end of the rotation connecting member 500 may be small or large.

Further, the position of the third rotation axis L3 at which the other end of the sub operation member 300 is coupled to the rotation connecting member 500 may be adjusted. That is, the length b may be formed to be small or large.

It is preferable that in the rotation connecting member 500 of the swing chair according to the present invention, the length a is large and the length b is small.

As discussed above, when the user applies the vertically pressing force F to the foothold 520 formed on the front side of the rotation connecting member 500, the force $F_x$ of rotating the rotation connecting member 500 is a/b*F*sin θ. Thus, as the length a becomes larger and the length b becomes smaller, the force $F_x$ of rotating the rotation connecting member 500 becomes larger even if the force F is small.

Thus, as the length a of the rotation connecting member 500 is formed to be larger and the length b of the rotation connecting member 500 is formed to be smaller, even when the user applies a small force to the foothold 520, the rotation connecting member 500 is rotated by a large force. As a result, the seat portion 400 in which the user is seated is easily moved forward.

As above, even when the user applies a small force to the foothold 520 using the principle of the lever, the seat portion 400 easily swing forward or rearward, so that the swing chair may be used for lower body exercise of the elderly person.

Referring to FIGS. 2 and 6, after the main operation member 200 and the seat portion 400 are moved forward, the main operation member 200 and the seat portion 400 are moved rearward in turn by the inertia while potential energy is converted into kinetic energy.

In this state, the rotation connecting member 500 is rotated in a direction in which the interior angle A of coupling between the rotation connecting member 500 and the main operation member 200 decreases. That is, the rotation connecting member 500 is rotated such that the interior angle A of coupling between the rotation connecting member 500 and the main operation member 200 is decreased to A−α, and the main operation member 200 and the seat portion 400 are interlocked with each other according to the virtual quadrangle and are moved rearward about the first rotation axis L1 with respect to the virtual vertical line.

Thereafter, the main operation member 200 and the seat portion 400 returns to original positions thereof again by the inertia, as illustrated in FIG. 5. In this case, because an inertia force becomes weak, the main operation member 200 and the seat portion 400 are moved less than the state illustrated in FIG. 5. That is, the rotation connecting member 500 is rotated by an angle that is smaller than the interior angle (A+α) of coupling between the rotation connecting member 500 and the main operation member 200.

Thus, at this time, when the user applies the pressing force F to the foothold 520 again, the force $F_x$ of lifting up the rear portion of the rotation connecting member 500 about the third rotation axis L3 increases, so that the rotation connecting member 500 is rotated by an angle that is larger than the state illustrated in FIG. 5. That is, the rotation connecting member 500 is rotated by an angle that is larger than the interior angle (A+α) of coupling between the rotation connecting member 500 and the main operation member 200. As a result, the seat portion 400 is moved greatly forward.

Through this process, the main operation member 200 and the seat portion 400 of the swing chair according to the present invention swing forward or rearward.

In short, when the user is seated in the seat portion 400 and applies the force to the foothold 520 in a state in which the swing chair is stopped as illustrated in FIG. 4, the seat portion 400 is moved forward as illustrated in FIG. 5, and the seat portion 400 is then moved rearward by the inertia as illustrated in FIG. 6. When the seat portion 400 is moved less than the state illustrated in FIG. 5 by the inertia, if the user applies the force to the foothold 520 again, the seat portion 400 continuously and greatly swings forward or rearward.

Because an inertial force increases after the main operation member 200 and the seat portion 400 swing, even when the user steps on the foothold 520 with a weak force in a state in which the seat portion 400 is moved forward, the seat portion 400 greatly swings.

As above, the swing chair according to the present invention easily swings even when a force is applied to the foothold 520 without a separate power source.

As in the present embodiment, when both the main operation member 200 and the sub operation member 300 installed on the front side of the main operation member 200 are formed in the shape of a wire, the seat portion 400 is installed not in the sub operation member 300 but in the main operation member 200.

If the seat portion 400 is installed in the sub operation member 300, when the user applies a force to the foothold 520 so that the rotation connecting member 500 is rotated about the third rotation axis L3, and thus the rear portion of the rotation connecting member 500 is lifted up, the main operation member 200 in the form of a wire is contracted and bent, and thus, the swing chair according to the present embodiment does not work.

Figure 7:
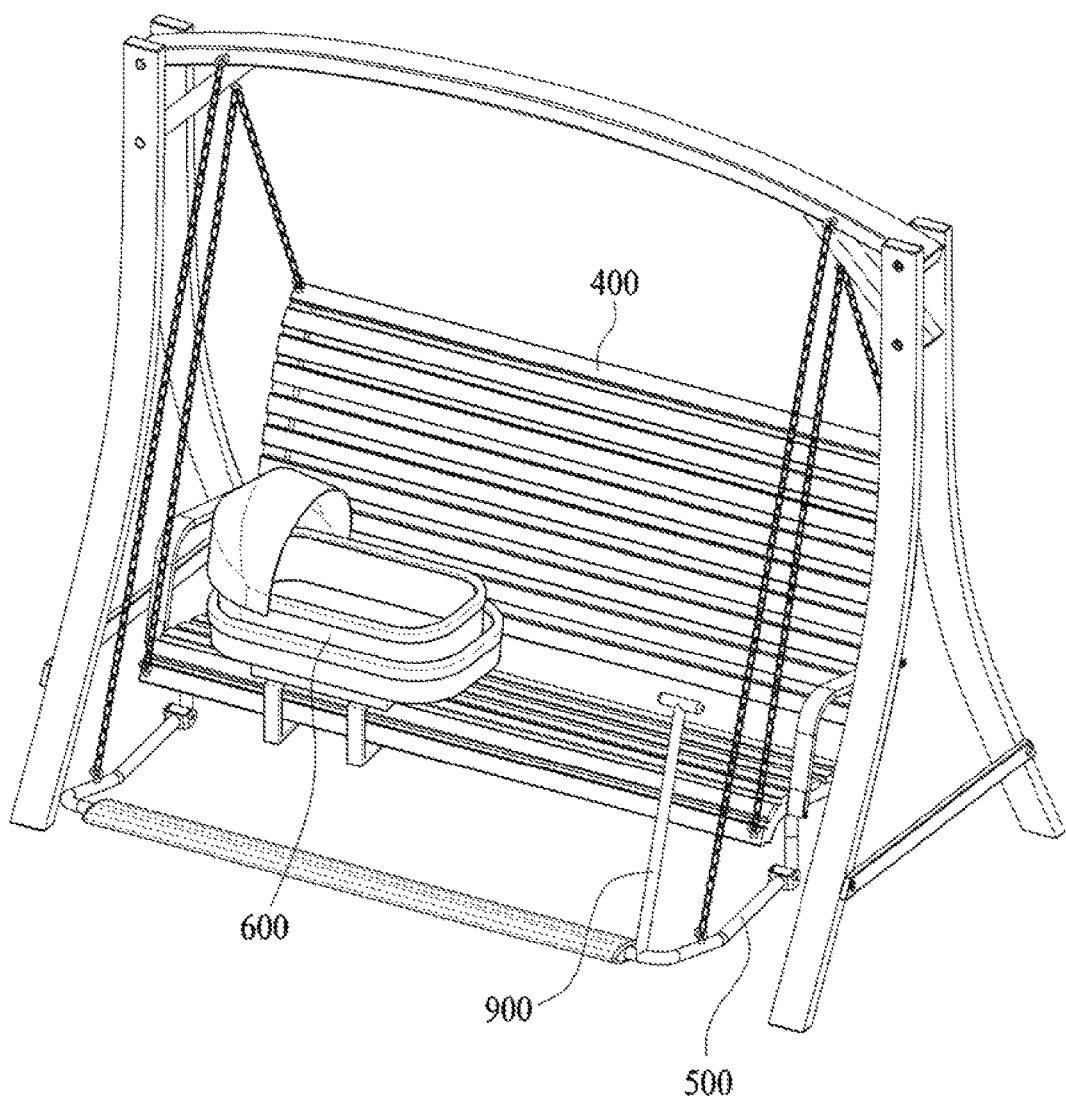
FIG. 7 is a view illustrating a state in which a cradle and a handle are provided in the swing chair according to the first embodiment of the present invention.

Referring to FIG. 7, a handle 900 may be further provided in the seat portion 400 or the rotation connecting member 500.

Thus, if the user is the child or the elderly person, when a guardian moves the handle 900 forward or rearward while gripping the handle 900, even if a force is not applied to the foothold 520, the seat portion 400 swings forward or rearward.

It is obvious that the shape of the handle 900 is not limited, and the handle 900 may be formed at various positions of the seat portion 400 or the rotation connecting member 500 in various forms.

It is preferable that a cradle 600 may be further provided in the seat portion 400, and the cradle 600 is fixedly installed in the seat portion 400 through a separate coupling means such that a baby does not fall.

In this case, in a state in which the young baby is laid in the cradle 600, the guardian may slowly swing the seat portion 400 while moving the handle 900 forward or rearward. Further, in a state in which the young baby is laid in the cradle 600, when the guardian is seated in the seat portion 400 and steps on the foothold 520 to swing the seat portion 400, the baby and the guardian may face each other, so that this is helpful in developing baby's emotion.

A separate operation handle (not illustrated) may be provided in the rotation connecting member 500 on the front side of the third rotation axis L3 serving as a point of coupling between the rotation connecting member 500 and the sub operation member 300. It is preferable that the operation handle may be replaced with the above-described handle 900, and may be arranged at a position which the user may access while being seated in the seat portion 400.

Thus, while being seated in the seat portion 400, the user may grip the operation handle (not illustrated) with hands without stepping on the foothold 520 to move the operation handle forward or rearward, so as to swing the seat portion 400 forward/rearward.

Figure 8:
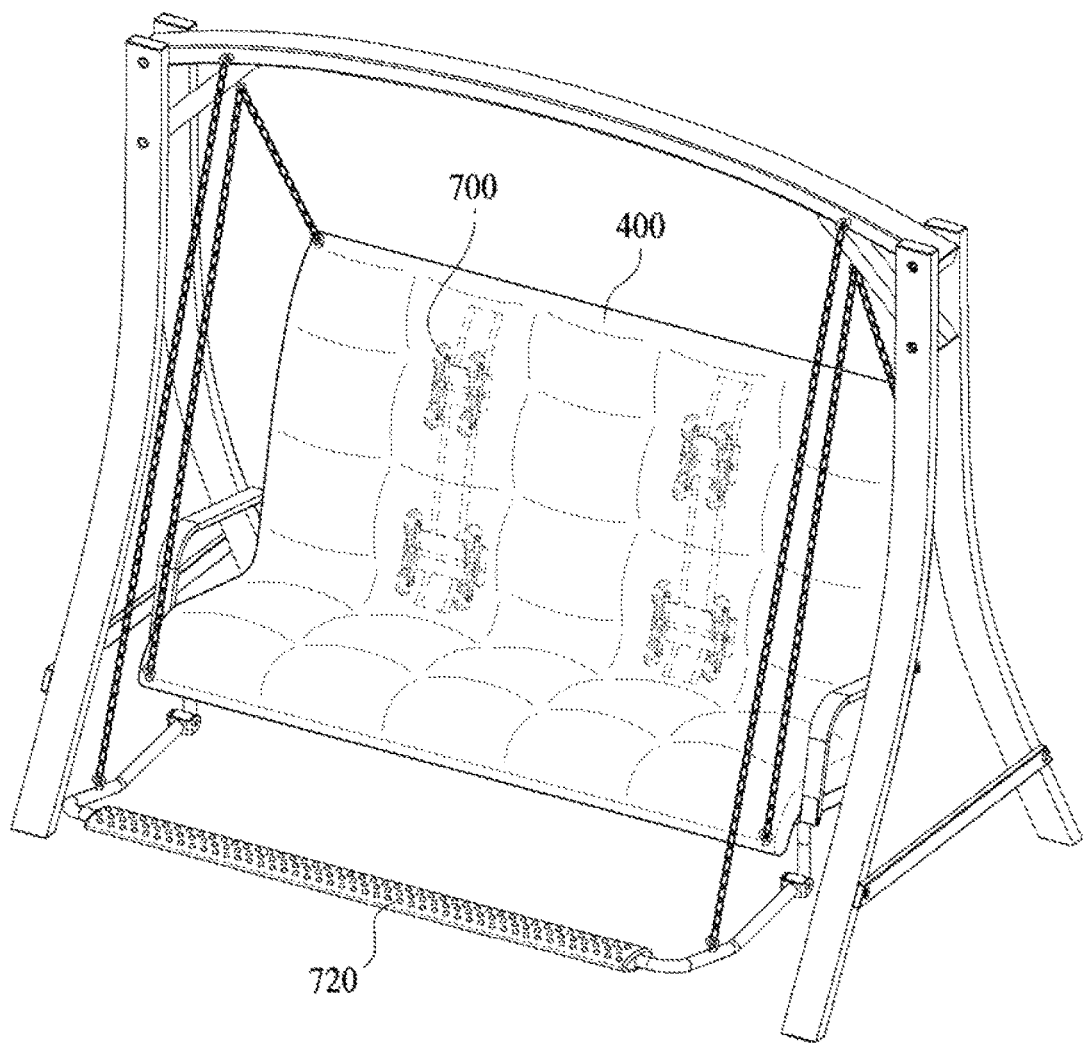
FIG. 8 is a view illustrating a state in which a massage means is provided in the swing chair according to the first embodiment of the present invention.

Referring to FIG. 8, the seat portion 400 or the rotation connecting member 500 may further include a massage means 700.

A vibration roller, a finger-pressure roller, or the like, which is electrically operated, may be used as the massage means 700, or a finger-press plate having a plurality of protrusions may be also used as the massage means 700.

In the embodiment, as illustrated in the drawing, a device having a massage function, such as the vibration roller and the finger-pressure roller which are electrically operated, may be embedded in the seat portion 400, and a finger-pressure pad (not illustrated) having a plurality of protrusions may be installed on the upper surface of the seat portion 400.

Further, as illustrated in the drawing, a finger-pressure plate 720 having a plurality of protrusions formed on the upper surface thereof may be installed instead of the foothold 520, and the electrically-operated finger-pressure roller (not illustrated) may be also installed.

Thus, while using the swing chair according to the present embodiment, the user may obtain an effect of receiving a massage.

Although not illustrated in the drawing, a means which may measure physical information may be further provided in the seat portion 400.

It is preferable that a means such as a small heart rate measuring device, a small body fat measuring device, a blood pressure measuring device for a watch, and a small calorie measuring device, which has a small volume and may simply measure the physical information, is used as the means which may measure the physical information.

Because the swing chair according to the present invention may easily swing even when the user steps on the foothold 520 with a weak force, when the elderly person uses the swing chair for the purpose of exercise, the elderly person may recognize a current health state using the physical information measuring means as well as may perform the exercise.

Hereinafter, configurations and operation schemes of the swing chair according to the second to sixth embodiments of the present invention will be described based on the fact that the sub operation member 300 is installed in the support 100 to be located on the front side of the main operation member 200.

Further, contents on the above-described operation structure of the swing chair illustrated in FIGS. 2 and 3 are commonly applied to the swing chair according to the second to sixth embodiments of the present invention, which will be described below.

Figure 9:
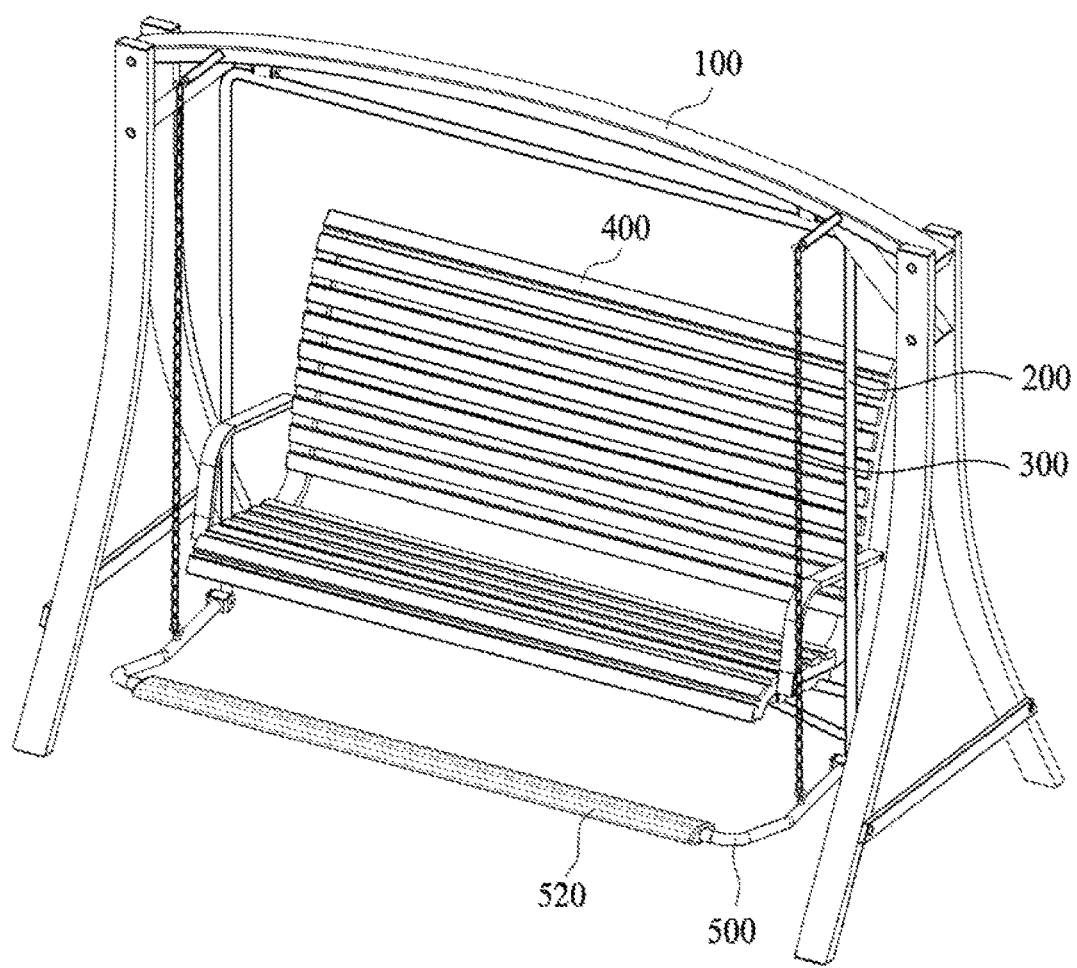
FIG. 9 is a view illustrating the entire shape of a swing chair according to the second embodiment of the present invention.
Figure 10:
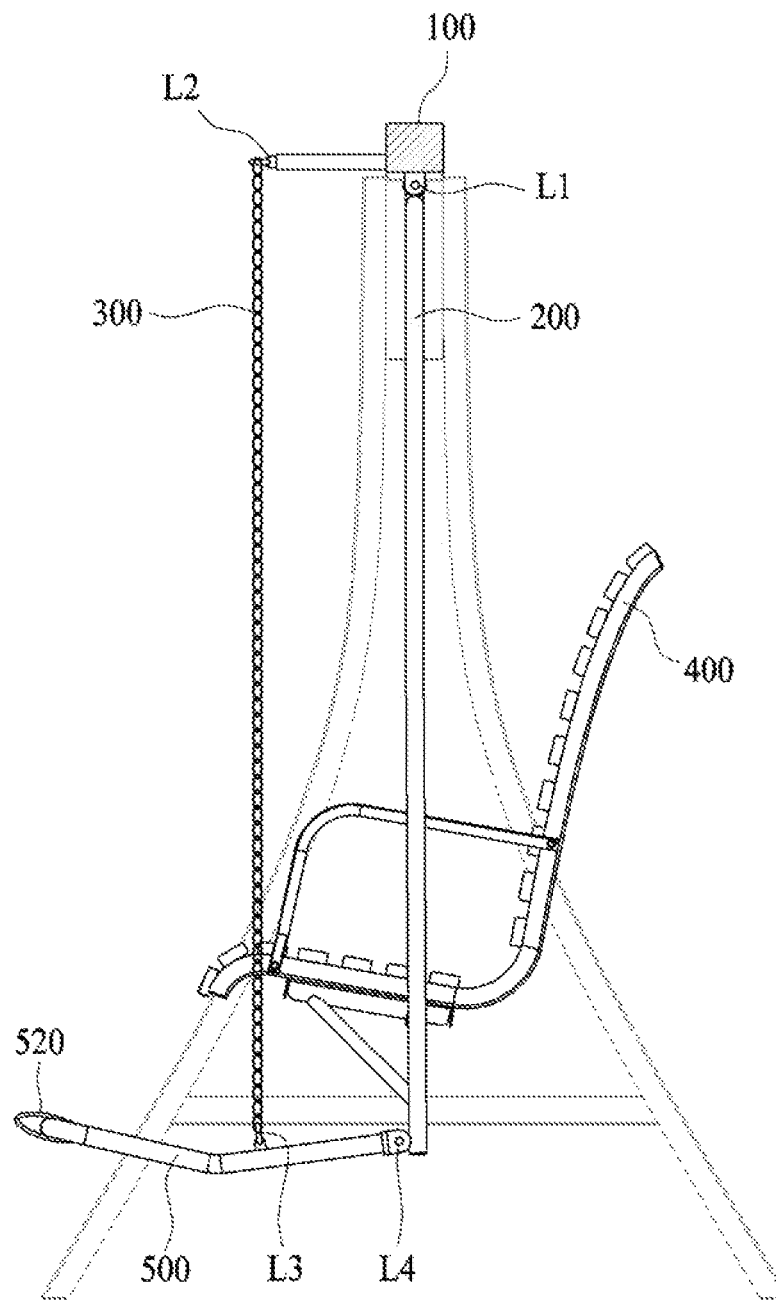
FIG. 10 is a side view illustrating the swing chair according to the second embodiment of the present invention.

FIGS. 9 to 10 are views illustrating the shape of the swing chair according to the second embodiment of the present invention.

The swing chair according to the second embodiment differs from the swing chair according to the first embodiment, which has been described in FIGS. 1 and 4 to 6, in that the main operation member 200 is formed in the shape of a rigid frame that is not bent.

As above, except for the configuration that the main operation member 200 is formed in the shape of a frame, configurations and an operation scheme of the swing chair according to the present embodiment are similar to the above-described configurations and the above-described operation scheme of the swing chair illustrated in FIGS. 2 to 6 according to the first embodiment.

Thus, when the user applies a force to the foothold 520, the seat portion 400 swings forward or rearward while the rotation connecting member 500 is rotated.

In the swing chair (not illustrated) according to the third embodiment, in FIGS. 9 and 10, the seat portion 400 is fixed and coupled to the spaced sub operation members 300 having the form of a wire through a separate coupling means.

In this way, when the seat portion 400 is fixed and coupled to the sub operation member 300 having the form of a wire through the separate coupling means, the user applies a force to the foothold 520 so that the rotation connecting member 500 is rotated about the third rotation axis L3. Thus, the main operation member 200 having the form of a frame is not bent even when the rear portion of the rotation connecting member 500 is lifted up, so that the swing chair according to the present embodiment swings forward/rearward.

The swing chair (not illustrated) according to the fourth embodiment differs from the swing chair illustrated in FIGS. 1 and 4 to 6 according to the first embodiment in that the sub operation member 300 is formed in the form of a frame.

Thus, even in the present embodiment, when the user steps on the foothold 520, the seat portion 400 swings forward and rearward, as illustrated in FIGS. 4 to 6.

In the above case, the seat portion 400 should be fixed and coupled not to the sub operation member 300 located on the front side and having the shape of a frame but to the main operation member 200 located on the rear side and having the shape of a frame.

If the seat portion 400 is coupled to the sub operation member 300, when the user applies a force to the foothold 520 to lift up the rear portion of the rotation connecting member 500, the main operation member 200 having the shape of a wire is bent and curved, and thus, the swing chair is not operated.

Figure 11:
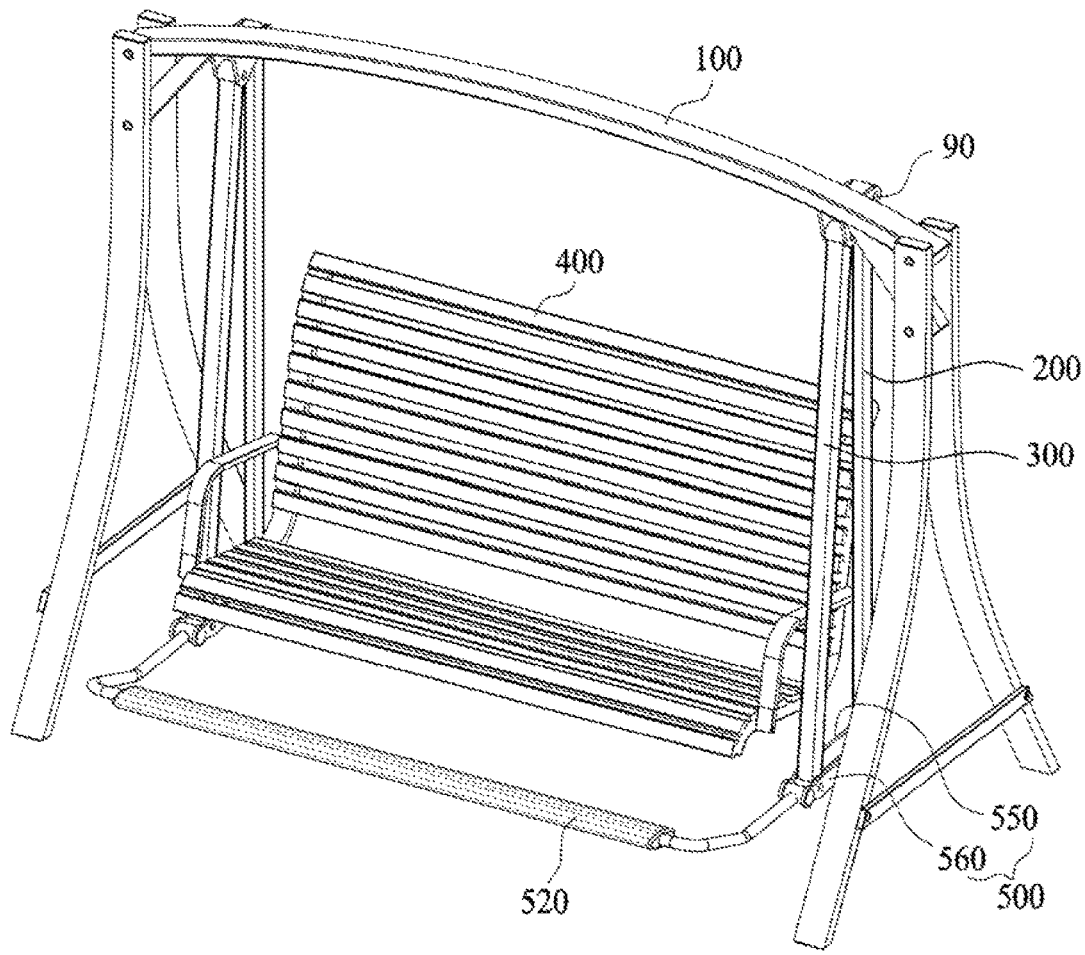
FIG. 11 is a view illustrating the entire shape of a swing chair according to the fifth embodiment and the sixth embodiment of the present invention.
Figure 12:
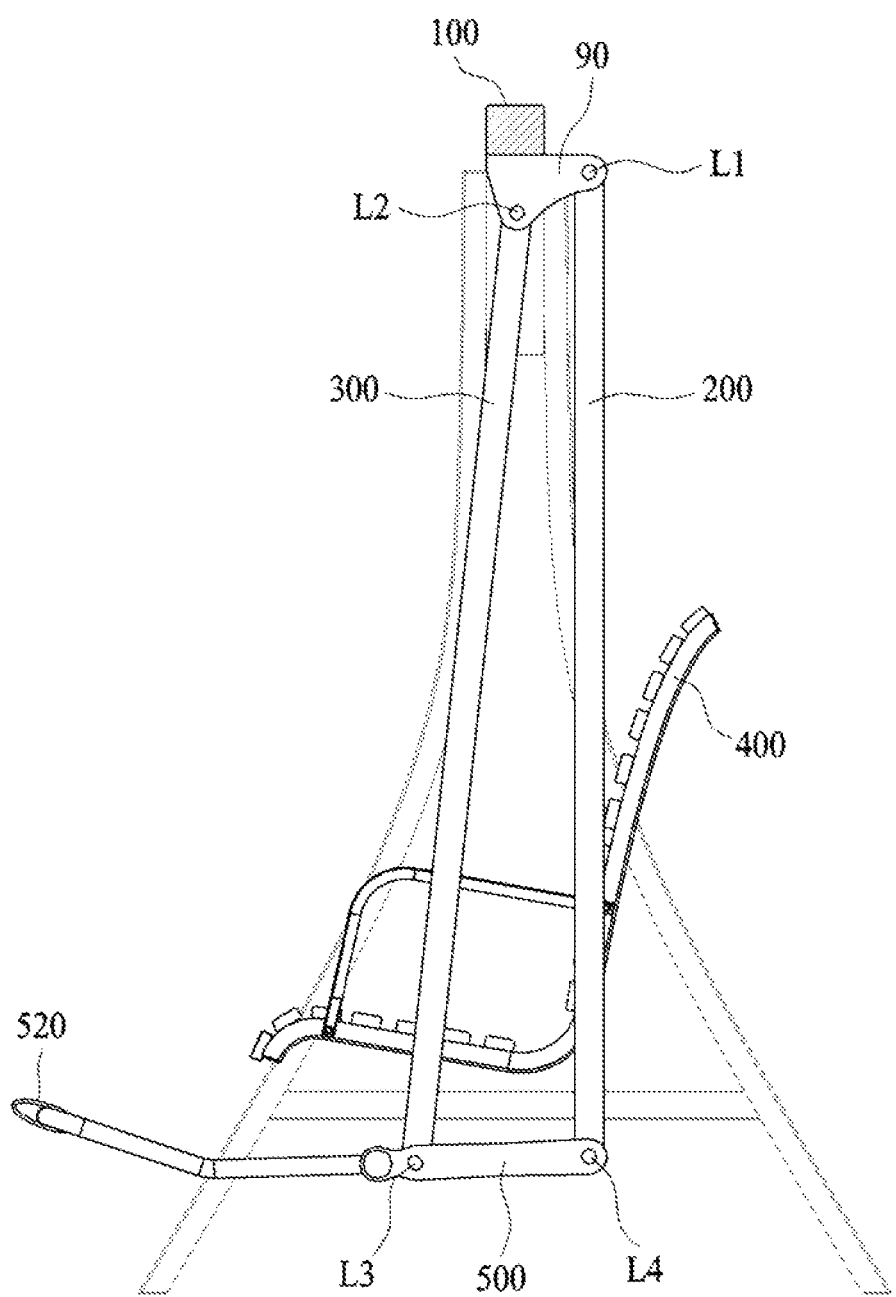
FIG. 12 is a side view illustrating the swing chair according to the fifth embodiment and the sixth embodiment of the present invention.

FIGS. 11 to 12 illustrate the shape of the swing chair according to the fifth embodiment and the sixth embodiment of the present invention.

The swing chair according to the present embodiment is formed in the shape of a rigid frame in which neither the main operation member 200 nor the sub operation member 300 are bent.

An upper portion of the main operation member 200 and an upper portion of the sub operation member 300 are rotatably coupled to each other through a connection means such as a bracket 90 installed in the support 100 to have the first rotation axis L1 and the second rotation axis L2, respectively.

Further, it is preferable that the first rotation axis L1 and the second rotation axis L2 are spaced apart from each other in a front-rear direction such that the upper portion of the main operation member 200 and the upper portion of the sub operation member 300 do not interfere with each other.

The rotation connecting member 500 rotatably coupled to the third rotation axis L3 and the fourth rotation axis L4 may include an inner plate 550 and an outer plate 560.

In the swing chair according to the fifth embodiment, the seat portion 400 is fixedly coupled to the main operation member 200, and in the swing chair according to the sixth embodiment, the seat portion 400 is fixedly coupled to the sub operation member 300.

Thus, even in the case of the swing chair according to the fifth embodiment and the sixth embodiment, when the user applies a force to the foothold 520, the seat portion 400 swings forward or rearward while the rotation connecting member 500 is rotated.

Hereinabove, the exemplary embodiments of the present invention have described above. It is obvious to those skilled in the corresponding art that the present invention may be specified in different specific forms in addition to the above-described embodiments without departing from the purpose and the scope of the present invention. Therefore, the above-described embodiments are considered to be not restrictive but illustrative, and accordingly, the present invention is not limited to the above descriptions and may be changed within the scope and equivalents of the appended claims.

The invention claimed is:

1. A swing chair comprising:
   a support which is installed at a certain height or more above a floor;
   a main operation member which is elongated and has a virtual first rotation axis provided to the support at one side thereof and which is rotatably coupled to the support;
   a sub operation member which is elongated and has a virtual second rotation axis, provided to the support at one side thereof and spaced parallel to the first rotation axis, and which is rotatably coupled to the support;
   a seat portion coupled to any one of the main operation member and the sub operation member; and
   a rotation connecting member which is elongated and arranged in a front-rear direction and has a rear portion that is rotatably coupled to the other side of the main operation member and a front portion that is rotatably coupled to the other side of the sub operation member so that a closed virtual quadrangle is formed together with the support, the main operation member, and the sub operation member,
   wherein an angle of coupling between the rotation connecting member and the main operation member is changed according to user's operation and the main operation member is interlocked with the virtual quadrangle and swings forward and backward based on the first rotation axis,
   wherein a portion of the rotation connecting member protrudes forward in a longitudinal direction,
   wherein the rotation connecting member is adjusted in a state in which a user is seated in the seat portion, and
   wherein a separate operation handle is provided in front of a point of coupling between the rotation connecting member and the sub operation member, so that the rotation connecting member is arranged at a position where the user approaches the rotation connecting member while being seated in the seat portion.

2. The swing chair of claim 1, wherein the rotation connecting member vertically swings about a point of coupling between the rotation connecting member and the sub operation member.

3. The swing chair of claim 2, wherein when an external force is applied to a front portion of the rotation connecting member to rotate the rotation connecting member rearward, an interior angle of coupling between the rotation connecting member and the main operation member increases in the virtual quadrangle.

4. The swing chair of claim 1, wherein a coupling position of the rotation connecting member and the sub operation member is adjusted along a longitudinal direction.

5. The swing chair of claim 1, wherein the rotation connecting member is extended and contracted forward along a longitudinal direction.

6. The swing chair of claim 1, wherein a front portion of the rotation connecting member along the longitudinal direction is formed in the shape of a foothold, so that the user operates the rotation connecting member using his/her foot while being seated in the seat portion.

7. The swing chair of claim 1, wherein at least a portion of the main operation member in the longitudinal direction is formed in the shape of a wire.

8. The swing chair of claim 7, wherein the seat portion is fixedly coupled to the main operation member.

9. The swing chair of claim 8, wherein an area of the main operation member, which is arranged below the seat portion along the longitudinal direction, is formed in the shape of a frame.

10. The swing chair of claim 8, wherein the sub operation member is formed in the shape of a wire.

11. The swing chair of claim 7, further comprising:
    a separate auxiliary support member which is elongated, and has one side that is connected to the support and the other side that is connected to the seat portion.

12. The swing chair of claim 11, wherein the auxiliary support member is formed in the shape of a wire.

13. The swing chair of claim 1, wherein the main operation member is formed in the shape of a frame, and
    wherein the sub operation member is formed in the shape of a wire.

14. The swing chair of claim 13, wherein the seat portion is fixedly coupled to a lower portion of the main operation member.

15. The swing chair of claim 13, wherein the seat portion is fixedly coupled to a lower portion of the sub operation member.

16. The swing chair of claim 1, wherein the main operation member is formed in the shape of a wire, and
    wherein the sub operation member is formed in the shape of a frame.

17. The swing chair of claim 16, wherein the seat portion is fixedly coupled to a lower portion of the main operation member.

18. The swing chair of claim 1, wherein the main operation member and the sub operation member are formed in the shape of a frame.

19. The swing chair of claim 18, wherein the first rotation axis and the second rotation axis are spaced apart from each other in a front-rear direction, and are coupled to the support.

20. The swing chair of claim 1, wherein a handle is further provided in at least one of the seat portion and the rotation connecting member.

21. The swing chair of claim 1, wherein the main operation member is provided in plurality, and the main operation members are spaced apart from each other on the first rotation axis, and
   wherein the seat portion is fixedly coupled between the main operation members.

22. The swing chair of claim 1, wherein the sub operation member is provided in plurality, and the sub operation members are spaced apart from each other on the second rotation axis, and
   wherein the seat portion is fixedly coupled between the sub operation members.

23. The swing chair of claim 1, wherein the seat portion further comprises a cradle.

24. The swing chair of claim 1, wherein the seat portion or the rotation connecting member further comprises a massage means.

25. The swing chair of claim 1, wherein the seat portion further comprises a means configured to measure physical information.

* * * * *